US010632288B2

(12) United States Patent  (10) Patent No.: US 10,632,288 B2
Spinoza  (45) Date of Patent: Apr. 28, 2020

(54) METHODS AND APPARATUS FOR SECURING A LINE

(71) Applicant: BRAIDLOCK LIMITED, London (GB)

(72) Inventor: Mark Spinoza, London (GB)

(73) Assignee: BRAIDLOCK LIMITED, London (GB)

( * ) Notice: Subject to any disclaimer, the term of this patent is extended or adjusted under 35 U.S.C. 154(b) by 500 days.

(21) Appl. No.: 14/604,099

(22) Filed: Jan. 23, 2015

(65) Prior Publication Data

US 2015/0141927 A1 May 21, 2015

Related U.S. Application Data

(63) Continuation of application No. 13/126,721, filed as application No. PCT/GB2009/051452 on Oct. 28, 2009, now Pat. No. 9,072,871.

(30) Foreign Application Priority Data

Oct. 28, 2008 (GB) .................................. 0819782.4

(51) Int. Cl.
*A61M 25/00* (2006.01)
*A61M 25/02* (2006.01)
(Continued)

(52) U.S. Cl.
CPC ............ *A61M 25/02* (2013.01); *A61M 39/10* (2013.01); *B65B 5/04* (2013.01); *A61M 5/1418* (2013.01);
(Continued)

(58) Field of Classification Search
CPC .......... A61M 25/02; A61M 2025/0206; A61M 2025/026; A61M 2025/0246; A61M 2025/024
See application file for complete search history.

(56) References Cited

U.S. PATENT DOCUMENTS 656,187 A    8/1900  Gunnel ..................... 285/148.13
2,017,625 A  10/1935 Kellems .................... 294/86.42
(Continued)

FOREIGN PATENT DOCUMENTS

DE    19522301    1/1997
EP    0009893     4/1980
(Continued)

OTHER PUBLICATIONS

Office Action dated Apr. 8, 2015 for corresponding European Application No. 14194602.0.
(Continued)

*Primary Examiner* — Scott J Medway
(74) *Attorney, Agent, or Firm* — Norton Rose Fulbright US LLP

(57) ABSTRACT

Methods and apparatus for securing a medical or surgical line with respect to a patient are described. In particular, a fastener is described comprising an elongate braided tubular sleeve for receiving the line therethrough, the sleeve having a first end for fixing adjacent to the patient, in use, and a second end for arranging, in use, proximal to medical equipment coupled to the line. The fastener also includes a first substantially rigid collar coupled to the sleeve at the first end of the sleeve and a second substantially rigid collar coupled to the sleeve at the second end of the sleeve. An enlarged flange is provided, secured to the first collar at the first end of the sleeve and an adhesive plaster for securing the fastener with respect to a patient is provided, the adhesive plaster being secured to the enlarged flange. In one embodiment, the adhesive plaster having an area of at least 5 cm². In addition, or in an alternative embodiment, the longitudinal axis of the elongate braided tubular sleeve is arranged parallel to the plane of the adhesive plaster.

13 Claims, 5 Drawing Sheets

(51) Int. Cl.
*A61M 39/10* (2006.01)
*B65B 5/04* (2006.01)
*A61M 5/14* (2006.01)

(52) U.S. Cl.
CPC ............. *A61M 2025/0206* (2013.01); *A61M 2025/026* (2013.01); *A61M 2025/0266* (2013.01); *A61M 2039/1066* (2013.01); *A61M 2207/00* (2013.01); *A61M 2209/06* (2013.01); *Y10T 29/49826* (2015.01)

(56) References Cited

U.S. PATENT DOCUMENTS

| | | | |
|---|---|---|---|
| 2,352,391 A | 6/1944 | Kitselman | 74/502.5 |
| 2,766,501 A | 11/1956 | Loyal | 294/86.42 |
| 3,122,806 A | 3/1964 | Lewis | 403/220 |
| 3,133,725 A | 5/1964 | Lanum | 254/134.3 |
| 3,368,564 A | 2/1968 | Selix | 604/180 |
| 3,487,837 A | 1/1970 | Petersen | 128/349 |
| 3,672,006 A | 6/1972 | Fidych | 24/122.6 |
| 3,883,102 A | 5/1975 | Trigg | 248/75 |
| 3,907,003 A | 9/1975 | Regner et al. | 138/118.1 |
| 4,221,215 A | 9/1980 | Mandelbaum | |
| 4,293,157 A | 10/1981 | Fidrych | 294/86.42 |
| 4,368,910 A | 1/1983 | Fidrych | 294/86.42 |
| 4,397,647 A | 8/1983 | Gordon | |
| 4,411,654 A | 10/1983 | Boarini et al. | 604/165.04 |
| 4,509,877 A | 4/1985 | Sobin et al. | 403/41 |
| 4,533,349 A | 8/1985 | Bark | 604/174 |
| 4,754,685 A | 7/1988 | Kite et al. | 87/9 |
| 4,865,583 A | 9/1989 | Tu | 605/508 |
| 4,867,154 A | 9/1989 | Potter et al. | 128/207.17 |
| 4,893,543 A | 1/1990 | Phillips | 87/34 |
| 4,906,234 A | 3/1990 | Voychehovski | 604/79 |
| 5,037,398 A | 8/1991 | Buchanan | |
| 5,038,663 A | 8/1991 | Plummer | 87/6 |
| 5,129,891 A | 7/1992 | Young | 604/533 |
| 5,147,322 A | 9/1992 | Bowen et al. | 604/180 |
| 5,152,298 A | 10/1992 | Kreyenhagen et al. | 607/116 |
| 5,188,101 A | 2/1993 | Tumolo | 128/207.18 |
| 5,201,357 A | 4/1993 | Kuhn et al. | 164/132 |
| 5,221,265 A | 6/1993 | List | 604/180 |
| 5,232,453 A | 8/1993 | Plass et al. | 604/180 |
| 5,257,975 A | 11/1993 | Foshee | 604/105 |
| 5,292,312 A | 3/1994 | Delk et al. | 604/180 |
| 5,306,256 A | 4/1994 | Jose | |
| 5,344,406 A | 9/1994 | Spooner | 604/179 |
| 5,344,415 A | 9/1994 | DeBusk et al. | 604/304 |
| 5,370,627 A | 12/1994 | Conway | 604/180 |
| 5,395,344 A | 3/1995 | Beisang et al. | 604/180 |
| 5,405,378 A | 4/1995 | Strecker | 623/1.12 |
| 5,429,608 A | 7/1995 | Rom et al. | |
| 5,437,650 A | 8/1995 | Larkin et al. | 604/536 |
| 5,460,170 A | 10/1995 | Hammerslag | 600/201 |
| 5,468,231 A | 11/1995 | Newman et al. | 604/180 |
| 5,476,493 A | 12/1995 | Muff | 607/119 |
| 5,480,203 A | 1/1996 | Favalora et al. | 294/86.42 |
| 5,501,216 A | 3/1996 | Byrd | |
| 5,505,117 A | 4/1996 | Dunlap et al. | 87/1 |
| 5,507,733 A | 4/1996 | Larkin et al. | 604/534 |
| 5,529,062 A | 6/1996 | Byrd | |
| 5,662,616 A | 9/1997 | Bousuet | 604/175 |
| 5,685,859 A | 11/1997 | Kornerup | 604/180 |
| 5,743,885 A | 4/1998 | Hoerby | 604/180 |
| 5,800,543 A | 9/1998 | McLeod et al. | 623/13.2 |
| 5,807,318 A | 9/1998 | St. Goar et al. | 604/508 |
| 5,807,341 A | 9/1998 | Heim | |
| 5,833,666 A | 11/1998 | Davis et al. | 604/180 |
| 5,836,913 A | 11/1998 | Orth et al. | 604/107 |
| 5,971,962 A | 10/1999 | Kojima et al. | |
| 6,319,231 B1 | 11/2001 | Andrulitis | |
| 6,471,676 B1 | 10/2002 | DeLegge et al. | |
| 6,702,789 B1* | 3/2004 | Owens | A61M 25/0111 128/200.16 |
| 7,344,558 B2* | 3/2008 | Lorenzo | A61B 17/12022 623/1.11 |
| 7,731,697 B2 | 6/2010 | Porter et al. | |
| 7,985,205 B2 | 7/2011 | Adams | |
| 8,361,034 B2* | 1/2013 | Spinoza | A61M 16/04 604/174 |
| 9,814,863 B2 | 11/2017 | Kyvik et al. | |
| 10,112,042 B2 | 10/2018 | Journot et al. | |
| 2007/0055205 A1* | 3/2007 | Wright | A61F 13/023 604/174 |
| 2016/0206856 A1 | 7/2016 | Watson | |

FOREIGN PATENT DOCUMENTS

| | | |
|---|---|---|
| EP | 0137880 | 4/1985 |
| EP | 0247571 | 12/1987 |
| EP | 0516876 | 12/1992 |
| EP | 0780138 | 6/1997 |
| EP | 1512640 | 3/2005 |
| GB | 2061372 | 5/1981 |
| GB | 1601334 | 10/1981 |
| GB | 2429154 | 2/2007 |
| JP | 55-16650 | 2/1980 |
| JP | 06-327776 | 11/1994 |
| JP | 10-248941 | 9/1998 |
| RU | 2033108 C1 | 4/1995 |
| SU | 1655512 A1 | 6/1991 |
| SU | 1836114 | 8/1993 |
| WO | WO 81/01519 | 6/1981 |
| WO | WO 82/03775 | 11/1982 |
| WO | WO 91/14034 | 9/1991 |
| WO | WO 92/06235 | 4/1992 |
| WO | WO 93/25264 | 12/1993 |
| WO | WO 95/29727 | 11/1995 |
| WO | WO 97/21459 | 6/1997 |
| WO | WO 98/52638 | 11/1998 |
| WO | WO 99/10250 | 3/1999 |
| WO | WO 01/13984 | 3/2001 |
| WO | WO 03/090835 | 11/2003 |
| WO | WO 03/105727 | 12/2003 |
| WO | WO2007/007043 | 1/2007 |
| WO | WO 10/049734 | 5/2010 |

OTHER PUBLICATIONS

"Communication pursuant to Article 96(2) EPC," Official action of the European Patent Office in European Application No. 04021343, dated Apr. 11, 2007.

Office Communication issued in U.S. Appl. No. 12/838,236, dated Sep. 28, 2011.

Office Communication issued in U.S. Appl. No. 12/838,236, dated Nov. 16, 2011.

Office Communication, issued in U.S. Appl. No. 09/506,361, dated May 22, 2002.

Office Communication, issued in U.S. Appl. No. 09/506,361, dated Aug. 1, 2002.

Office Communication, issued in U.S. Appl. No. 09/506,361, dated Apr. 8, 2003.

Office Communication, issued in U.S. Appl. No. 09/506,361, dated Jan. 9, 2004.

Office Communication, issued in U.S. Appl. No. 09/506,361, dated Mar. 12, 2004.

Office Communication, issued in U.S. Appl. No. 09/506,361, dated Jul. 13, 2005.

Office Communication, issued in U.S. Appl. No. 09/506,361, dated Dec. 1, 2005.

Office Communication, issued in U.S. Appl. No. 09/506,361, dated Jun. 5, 2006.

Office Communication, issued in U.S. Appl. No. 09/506,361, dated Nov. 29, 2007.

Office Communication, issued in U.S. Appl. No. 09/506,361, dated Jun. 24, 2008.

Office Communication, issued in U.S. Appl. No. 09/506,361, dated Dec. 29, 2008.

(56) References Cited

OTHER PUBLICATIONS

Office Communication, issued in U.S. Appl. No. 09/506,361, dated Jun. 11, 2009.
Office Communication, issued in U.S. Appl. No. 09/506,361, dated Mar. 25, 2010.
Office Communication, issued in United Kingdom Patent Application No. GB0514424.1, dated Mar. 10, 2010.
Office Communication, issued in United Kingdom Patent Application No. GB0819782.4, dated Feb. 9, 2009.
Office Communication, issued in U.S. Appl. No. 11/995,492, dated Mar. 17, 2011.
Office Communication, issued in U.S. Appl. No. 11/995,492, dated Nov. 22, 2011.
PCT International Search Report and Written Opinion issued in International application No. PCT/GB2009/051452, dated Oct. 22, 2010.
Office Communication issued in European Application No. 09 760 280.9, dated Feb. 15, 2013.

* cited by examiner

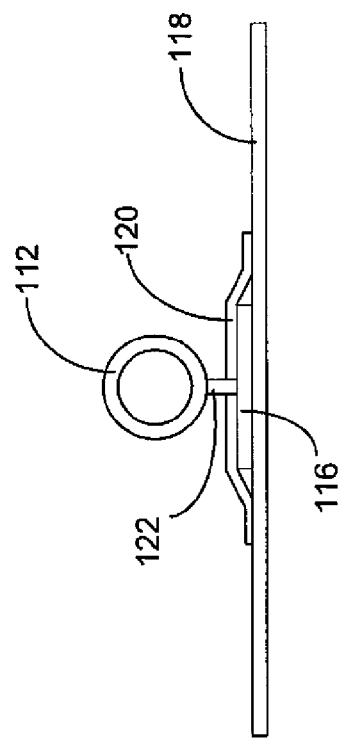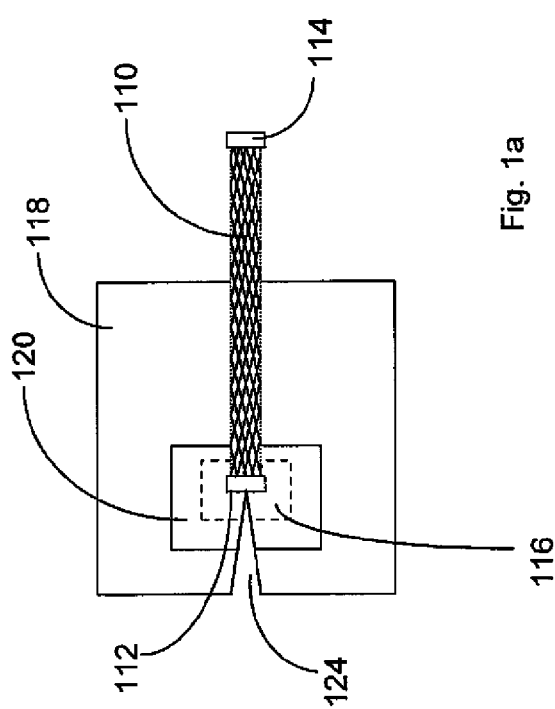

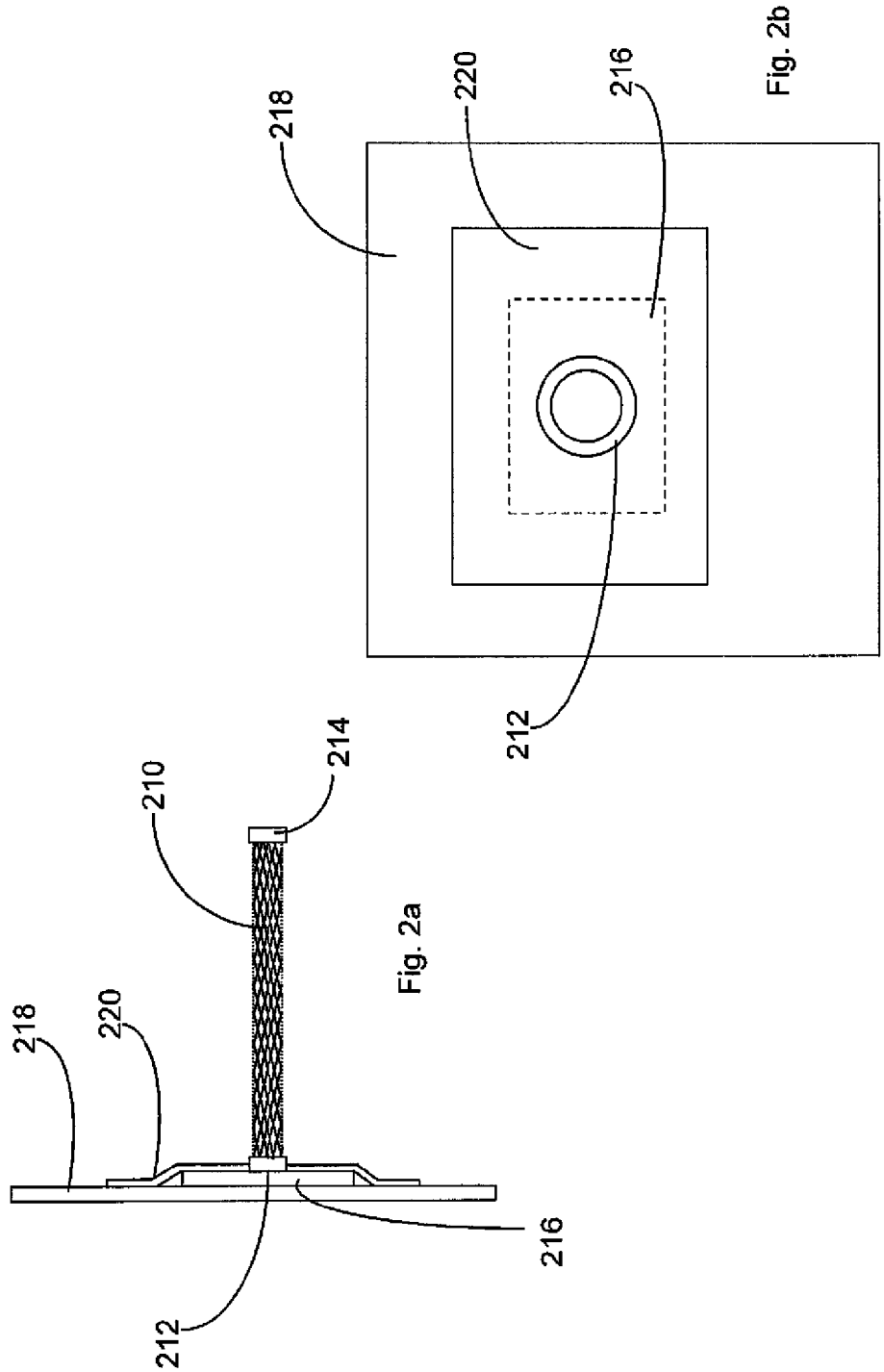

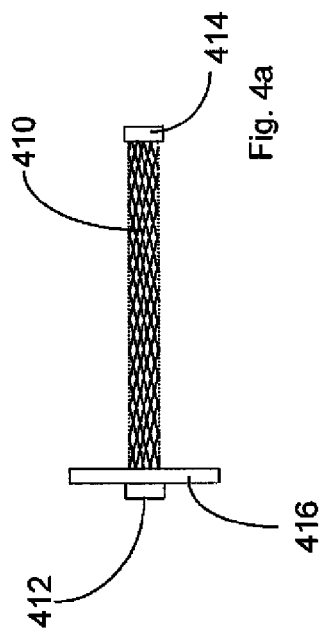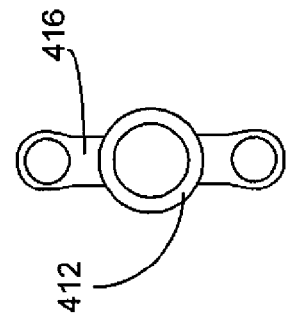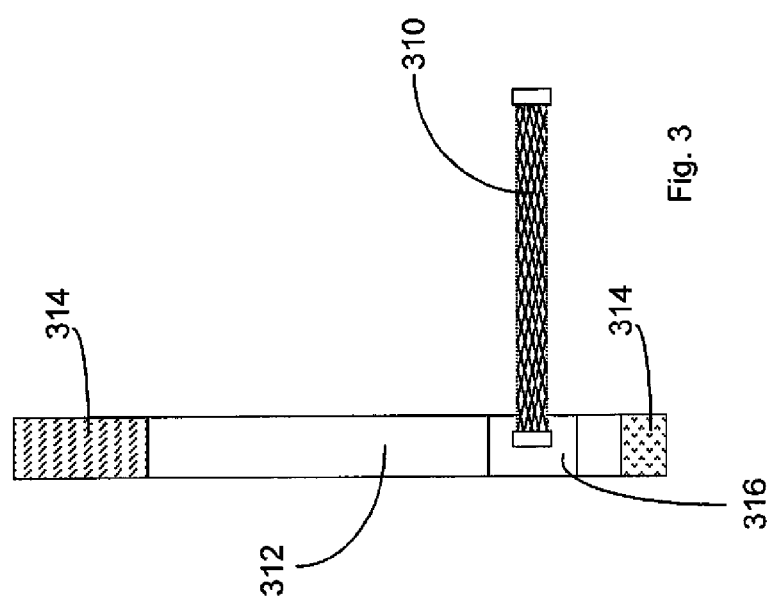

METHODS AND APPARATUS FOR SECURING A LINE

This application is a continuation of co-pending U.S. patent application Ser. No. 13/126,721 filed Sep. 30, 2011, which is a national phase application under 35 U.S.C. § 371 of International Patent Application No. PCT/GB2009/051452 filed Oct. 28, 2009 which claims priority to UK Patent Application No. GB 0819782.4 filed Oct. 28, 2008. The entire text of each of the above-referenced disclosures are specifically incorporated herein by reference without disclaimer.

The present invention relates broadly to the field of fasteners and is particularly concerned with medical or surgical fasteners that secure lines, such as catheters, other types of medical tubing or wires with respect to a patient.

By way of background, catheters are long, thin, flexible tubes of plastics material that can be inserted into a blood vessel or other body cavity for introducing or removing fluids; either liquids or gases. They are used by medical personnel as a matter of routine. In one medical procedure a line or catheter is secured with respect to a patient, for example medical tubing may be secured to a patient's arm, and in another procedure an endotracheal tube may be secured to ventilate a patient. In both cases, it is desirable that, once the line has been inserted, it is securely maintained in position unless a medical practitioner wishes to adjust the positioning of the line.

The insertion of a catheter into a patient is an intricate procedure. Therefore, once a line is in an acceptable position, it is essential that the line is securely anchored to avoid any accidental displacement. The line may need to be in place for a period of weeks: the longer a line remains undisturbed in situ in accordance with planned treatment, the lower the risk of harm to the patient. Similarly, the insertion of an endotracheal tube can be a time-consuming and difficult procedure. Again, it is essential that, once inserted, such tubes are securely fastened in position to avoid potential problems and complications for the patient.

The applicant's earlier application, published as WO-A1-99/10250 describes an improved fastener for securing a line to a patient including a braided sleeve portion for gripping a line and means for attaching the sleeve with respect to a patient. This application was largely directed to embodiments in which the sleeve is sutured to a patient or attached via a harness.

The present invention provides improved devices for securely maintaining a line in position with respect to a patient.

A first aspect provides a fastener for securing a medical or surgical line with respect to a patient, the fastener comprising:
  an elongate braided tubular sleeve for receiving the line therethrough, the sleeve having a first end for fixing adjacent to the patient, in use, and a second end for arranging, in use, proximal to medical equipment coupled to the line;
  a first substantially rigid collar coupled to the sleeve at the first end of the sleeve;
  a second substantially rigid collar coupled to the sleeve at the second end of the sleeve;
  an enlarged flange secured to the first collar at the first end of the sleeve;
  an adhesive plaster for securing the fastener with respect to a patient, the adhesive plaster being secured to the enlarged flange and the adhesive plaster having an area of at least 5 cm$^2$.

It has been appreciated that providing a fastener with a sleeve and an adhesive plaster enables rapid, reliable and secure fixing of a line with respect to a patient. No suturing or complicated connection of the sleeve is required, therefore it can be fixed in place by non-specialists, such as nurses, paramedics and first-aid practitioners. Also, it can be used in a wide range of settings, such as for the fixation of a drip in a non-medical setting, for example in a military situation, on the street, or at a sporting match.

It has been found that the claimed combination of an enlarged flange secured to a collar at one end of the sleeve and an adhesive plaster having an area of at least 5 cm$^2$, wherein the flange is secured to the adhesive plaster, provides secure attachment of the line to the patient. The adhesive plaster should be large enough to provide an adhesive force to the patient greater than forces that are applied to the line during normal movement of a patient or forces applied by the patient tugging the line. Providing an enlarged flange advantageously enables a secure connection between the braided tubular sleeve and the adhesive material.

In a preferred embodiment, the longitudinal axis of the elongate braided tubular sleeve is arranged parallel to the plane of the adhesive plaster.

In an alternative embodiment, the longitudinal axis of the elongate braided tubular sleeve is arranged perpendicular to the plane of the adhesive plaster. That is, the plane of the flange is parallel to the face of the collar to which it is attached. This arrangement is useful where the line needs to be held perpendicular to the patient's skin. For example at the point at which a chest drain enters the patient.

In a second aspect, there is provided a fastener for securing a medical or surgical line with respect to a patient, the fastener comprising:
  an elongate braided tubular sleeve for receiving the line therethrough, the sleeve having a first end for fixing adjacent to the patient, in use, and a second end for arranging, in use, proximal to medical equipment coupled to the line;
  a first substantially rigid collar coupled to the sleeve at the first end of the sleeve;
  a second substantially rigid collar coupled to the sleeve at the second end of the sleeve;
  an enlarged flange secured to the first collar at the first end of the sleeve;
  an adhesive plaster for securing the fastener with respect to a patient, the adhesive plaster being secured to the enlarged flange;
  wherein the longitudinal axis of the elongate braided tubular sleeve is arranged parallel to the plane of the adhesive plaster.

In this embodiment, the plane of the flange is perpendicular to the face of the collar to which it is attached. This arrangement of the sleeve and plaster is particularly suitable for situations in which the line needs to be held parallel to a patient's skin, for example when an intravenous drip is inserted into a patient. Arranging the sleeve to be held parallel to the adhesive plaster reduces the forces that act against the adhesive force of the plaster. For example, a tugging force applied to the line acts as a sheer force on the adhesive plaster rather than acting in a perpendicular direction, which would make the plaster easier to remove.

In a preferred embodiment, the adhesive plaster has an area of at least 5 cm$^2$.

In a preferred embodiment of the first and second aspects, the enlarged flange is coupled to a first layer of adhesive plaster by a second layer of adhesive plaster, the second layer of adhesive plaster being arranged over the enlarged flange. That is, the flange is sandwiched between two layers of adhesive plaster, thus securely retaining the flange on the first layer of adhesive plaster. This embodiment also minimises the types of materials required to manufacture the fastener and simplifies the manufacturing process. Preferably, the second layer of adhesive plaster is larger than the area of the flange by at least around 0.5 cm in each direction, preferably at least around 1 cm.

In one embodiment, the enlarged flange has an area of at least 1 cm$^2$. In a further embodiment, the enlarged flange has an area of at least 2 cm$^2$.

In one embodiment, the adhesive plaster has an area of at least 10 cm$^2$. In a further embodiment, the adhesive plaster has an area of at least 20 cm$^2$. The area of the plaster may depend on factors such as the intended use of the fastener, the size of the patient, the adherence of the surface onto which the fastener is applied and the length of time the fastener is expected to be attached to the patient.

In a preferred embodiment, the enlarged flange and the first collar are manufactured using a common material. The material may comprise a plastics material, such as polypropylene or polyamide. Such materials are easy to mould or extrude to form into a suitable shape and can be made sterile for medical purposes.

In one embodiment, the enlarged flange is coupled to the first collar using at least one technique selected from: ultrasound welding; high-frequency welding; and heat-sealing.

In particular, ultrasound welding techniques have been found to be particularly advantageous in providing secure attachment between components of the fastener, for example between the collar and the flange.

In an alternative embodiment, the flange is moulded integrally with the collar. In this way, the flange and the collar may be moulded as a single piece, providing a very secure attachment between the collar and the flange. The piece may be moulded using any suitable moulding technique, in particular the piece may be injection-moulded.

In a preferred embodiment, the adhesive plaster comprises a sterile medical or surgical plaster. Once formed, the fastener may be provided in a sterile pack in which it is transported and handled up to the point at which the pack is opened for use.

In one embodiment, the plaster comprises a pre-applied adhesive coating. The plaster will therefore also include backing paper or plastic, which can be removed from the plaster to reveal the adhesive coating before it is applied to the patient.

In an alternative embodiment, an adhesive coating is applied to the plaster prior to the plaster being secured to the patient, for example a medial practitioner may spray an adhesive coating onto the plaster or the patient and then press the plaster onto the sprayed coating.

In a preferred embodiment, the braided tubular sleeve comprises a plurality of braided strands.

Preferably, each collar is sealed to each of the strands at an end of the braided tubular sleeve. Hence the collar may be sealed to the strands of the sleeve to secure the strands and avoid any fraying of the braiding of the sleeve. Preferably, the strands are sealed to the sleeve using adhesive or a welding technique, in particular ultrasound welding.

The collars enable a user to manipulate the ends of the sleeve; in particular if the collars are pushed towards each other, the sleeve is shortened and widened and the sleeve is able to slide along the line. The collars can also be used to maintain an open aperture at each end of the sleeve to enable easy insertion of the line into the sleeve.

In a preferred embodiment, the adhesive plaster comprises a pre-formed cut-out adjacent to the first end of the elongate braided tubular sleeve. That is, there is a cut-out in the plaster at the end of the sleeve where the line interfaces with the patient. The cut-out may be an aperture through which the line can pass, or may be a missing portion of the plaster. The cut-out enables access to the patient's skin at a point that would otherwise be covered by plaster. The cut-out may also enable the point at which the line interfaces with the patient to be positioned closer to the point at which the line exits the tubular sleeve at the first collar, thus providing a more secure connection between the line in the sleeve and the patient.

In a preferred embodiment, the lateral force required to separate the adhesive plaster from the patient, applied substantially parallel to the longitudinal axis of the elongate braided tubular sleeve, is greater than 1N.

Further preferably, the lateral force required to separate the adhesive plaster from the patient, applied substantially parallel to the longitudinal axis of the elongate braided tubular sleeve, is greater than 5N.

In some embodiments, the lateral force required to separate the adhesive plaster from the patient, applied substantially parallel to the longitudinal axis of the elongate braided tubular sleeve, is greater than 10N.

In a further aspect, there is provided a method of manufacturing a plurality of fasteners for securing a medical or surgical line with respect to a patient, the method comprising:

providing a supply of a braided tubular sleeve having a length of at least one metre;

providing a braided tubular sleeve portion from the supply, the portion substantially having a selected length of less than 15 cm;

providing a collar around each end of the braided tubular sleeve portion; and sealing each end of the braided tubular sleeve portion within each respective collar to form a first fastener;

repeating said providing to form at least one further fastener.

Preferably, the method further comprises separating the braided tubular sleeve portion from the supply. The portion may be separated from the supply before the collars are attached to the sleeve.

In an alternative embodiment, the braided tubular sleeve portion is separated after sealing the braided tubular sleeve portion within the collars. This may prevent fraying or unravelling of the sleeve before the collar is fixed in place.

In a preferred embodiment, the braided tubular sleeve portion comprises a braid of a plurality of strands of material and sealing the braided tubular sleeve portion within each collar comprises sealing each of the strands of material to each collar.

Preferably, sealing the braided tubular sleeve portion within each collar comprises at least one of:

ultrasound welding the braided tubular sleeve portion to the collar;

high-frequency welding the braided tubular sleeve portion to the collar; and heat-sealing the braided tubular sleeve portion to the collar.

In particular, ultrasound welding has been found to be a particularly advantageous technique for sealing the strands of the braided tubular sleeve portion to the collar. This technique has been found to provide reliably a secure connection between each of the strands and the collar, which prevents unravelling of the braid and enables the collars to be used to compress the sleeve portion.

A medical or surgical apparatus comprising a sealed sterile pack containing:
  a tube for supplying a fluid to or removing a fluid from a patient;
  a connector positioned at each end of the tube; and
  a braided tubular sleeve surrounding the tube and positioned between the connectors, the braided tubular sleeve comprising a substantially rigid collar at each end of the sleeve;
  wherein pushing the collars towards each other along the longitudinal axis of the sleeve shortens and widens the sleeve, allowing the sleeve to slide along the tube;
  wherein the sleeve is biased to an elongate position so that releasing the collars causes the sleeve to lengthen and grip the tube;
  wherein the maximum diameter of each connector is greater than the internal diameter of each of the collars so that the collars do not fit over either connector and the braided tubular sleeve is retained on the tube.

A method of forming a medical or surgical apparatus comprising:
  providing a tube for supplying a fluid to or removing a fluid from a patient;
  sliding a braided tubular sleeve onto the tube, wherein the braided tubular sleeve comprises a substantially rigid collar at each end of the sleeve and wherein sliding comprises:
  pushing the collars towards each other along the longitudinal axis of the sleeve to shorten and widen the sleeve;
  sliding the sleeve onto the outer surface of the tube;
  releasing the collars to enable the sleeve to return to a biased elongate position, causing the sleeve to grip the tube;
  attaching a connector to each end of the tube, wherein the maximum diameter of each connector is greater than the maximum internal diameter of either collar so that the collars do not fit over either connector and the braided tubular sleeve is retained on the tube; and
  sealing the apparatus within a sterile container.

Providing a pre-formed set, which may be termed a "giving set", including a fastener already threaded onto a collar may provide a convenient way of attaching a tube to a patient. Since the fastener cannot fit over the connectors at either end of the tube, the fastener is securely attached to the tube and, via the fastener, the tube is securely attached to the patient.

The fastener may be secured to the patient using sutures, and suture loops may be provided in the fastener for this purpose. Alternatively, the fastener may be secured with respect to the patient using an adhesive plaster as described above.

Embodiments of the present method and apparatus will now be described in more detail with reference to the accompanying drawings in which:

FIGS. 1a and 1b are schematic illustrations of a fastener according to one embodiment in plan view and a cross-sectional view respectively;

FIGS. 2a and 2b are schematic illustrations of a fastener according to a further embodiment in plan view and a cross-sectional view respectively;

FIG. 3 is a schematic illustration of a fastener according to a further embodiment;

FIGS. 4a and 4b are schematic illustrations of a fastener according to a further embodiment in plan view and a cross-sectional view respectively;

Figure 5:
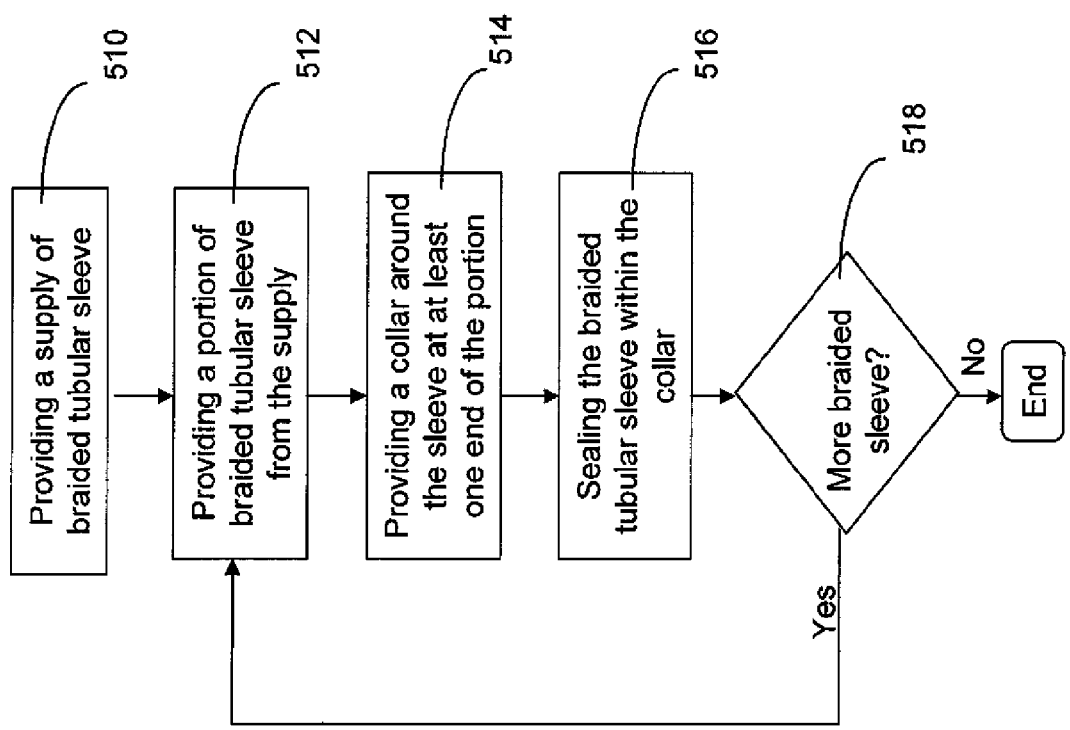
FIG. 5 is a flow chart representing a method of manufacture of a fastener according to one embodiment.

A fastener according to one embodiment includes a braided tubular sleeve comprising a plurality of strands of helically-wound and interwoven or intertwined filaments of polyamide or Nylon™. The wall of the sleeve may therefore be described as being braided or plaited to form a foraminous or perforated mesh, grid, net or web. Thus the wall defines numerous small openings between the strands of the braid, which expand or contract as the sleeve is shortened and lengthened.

A collar is provided at each end of the sleeve. Each collar is formed separately from the sleeve and is then placed around one of the ends of the sleeve and fixed to the strands that form the sleeve. The collar is also formed from a plastics material, in this embodiment, also from polyamide.

As described in more detail below, the collar is fixed to the strands of the sleeve using an ultrasound welding technique.

It will be appreciated that, due to the braided construction of the sleeve, the length of the sleeve can be varied by the application of a compression or tension force along the longitudinal axis of the sleeve. It will further be appreciated that elongation causes the sleeve to narrow, whereas shortening the sleeve makes it wider.

Shortening of the sleeve causes the filaments of the braid to bunch together and to lie at a large angle with respect to the longitudinal axis of the sleeve. Therefore, when the sleeve is shortened, the diameter of the aperture formed by the sleeve is at a maximum. In contrast, elongation of the sleeve causes the filaments of the braid to lie at a smaller angle with respect to the longitudinal axis of the sleeve. Hence, the diameter of the aperture formed by the sleeve is at a minimum.

The sleeve is biased to a slightly elongated position so that the diameter of the braided sleeve is slightly narrower than the diameter of the aperture at each end formed by the collars. Therefore, when a tube or line having a similar size diameter to that of the aperture formed by a collar is inserted through the sleeve, the sleeve is biased to grip the tube or line.

It will be appreciated that, once the initial grip of the sleeve around the line is established, further attempts to move the line axially with respect to the sleeve will cause further longitudinal expansion forces to be applied to the sleeve, hence causing the sleeve to narrow further and grip the line more tightly. This gives rise to a locking effect. However, it is further noted that release of the line is possible simply by longitudinally compressing the sleeve to cause the diameter of the sleeve to widen and release the line. This longitudinal compression may be achieved by moving at least one of the collars towards the middle of the sleeve. Adjustments to the line may then be made by sliding the line within the sleeve and the line may then be gripped again by releasing the sleeve and allowing the sleeve to return to its expanded configuration.

It will be clear to the skilled person that many variations in design and construction of the fastener may be provided and some of the designs that have been found to be particularly advantageous are described in more detail below.

In some embodiments, the braid may be manufactured from other types of material, in particular other types of plastic, such as polypropylene. Similarly, the collars may also be manufactured from other types of plastic, such as polypropylene or they may be manufactured using a metal material.

Plastics or metal materials are particularly suitable for components of the fastener, since they may readily be sterilised for medical or surgical use and can easily be moulded and joined together. Further, it may simply the manufacturing to have the braid and the collar formed from the same material.

In one embodiment, the collar may be formed, at least in part, using the plastic of the sleeve. For example, the plastic strands of the sleeve may be heat-sealed or ultrasound welded together over a short distance at the end of the sleeve to form a solid collar at each end of the sleeve. In this case, a separate collar may not be necessary.

In alternative embodiments, the collar may be fixed to the end of the sleeve using an alternative technique or a combination of techniques, such as heat-sealing, high-frequency welding, adhesive or by physically trapping the strands of the sleeve between two concentric layers of the collar.

A specific embodiment of a fastener will now be described in more detail with reference to FIGS. 1a, 1b, 2a and 2b.

The fastener of FIG. 1a includes a braided tubular sleeve 110, having a collar at each end 112, 114. At one end of the sleeve 110, one of the collars 112 is secured to a flange 116. As illustrated in FIG. 1b, the collar 112 is secured to the flange 116 via an arm portion 122. The arm portion 122 lifts the collar 112 away from the surface of the flange 116, enabling the flange 116 to be secured more easily to the attachment means, as described below.

In this embodiment, the collar 112, the arm 122 and the flange 116 are moulded in one piece. Therefore, the collar 112 is very securely attached to the flange 116.

At each end, the braided sleeve 110 passes inside a collar 112, 114. The strands that make up the sleeve 110 are secured to each of the collars 112, 114 using ultrasound welding. Therefore, each strand of the sleeve 110 is securely attached to each collar 112, 114, preventing any fraying or unravelling of the sleeve.

To attach the fastener to a patient, the flange is secured to a plaster 118. The back of the plaster 118 comprises an adhesive material with sufficient adhesion to secure the plaster to a patient's skin. The plaster 118 is provided with backing paper or plastic, which is removed by a medical practitioner when the fastener is in position and the practitioner wishes to secure the fastener to the patient.

The flange 116 is secured to the plaster using a second layer of plaster 120, which is placed over the top of the flange 116 and onto the first plaster layer 118, as illustrated in FIG. 1b.

The second layer of plaster 120 extends over the edges of the flange 116 by about 1 cm in each direction to ensure a secure connection of the flange 116 to the first layer of plaster 118.

The first layer of plaster 118 includes a cut-out section 124 which enables a line emerging from the sleeve 110 to have direct access to the patient's skin. The cut-out 124 may take many shapes and forms, for example it may be a hole through which the line can pass. Alternatively, the collar 112 and flange 116 may be arranged at the edge of the plaster 118 so that the line has access to the patient directly without the need for a cut-out section.

In some embodiments, the collar 112 is secured to the arm 122 and the arm 122 is secured to the flange 116 using ultrasound welding technique as described below. The collar 112, the arm 122 and the flange 116 are all formed from the same material, in this embodiment polyamide.

In alternative embodiment, the arm 122 may be omitted and the collar 112 may be secured directly to the flange 116. In this embodiment, the second adhesive material 120 may still be fitted around the collar 112 and over the flange 116, but it may be more difficult to secure the material 120 to the flange 116 around the collar 112.

As an alternative to the use of the second layer of plaster 120, the flange 116 may be connected to the first plaster layer 118 using welding or heat sealing techniques or another fixing mechanism, such as small rivets, which may also be made from plastic.

An alternative embodiment of the fastener secured by a plaster is illustrated in FIG. 2a and this embodiment also includes the braided tubular sleeve 210 with collars 212, 214, one of which is secured or integrally moulded with a flange 216. The flange 216 is secured to a first layer of adhesive plaster 218 by a second layer of adhesive plaster 220 that is placed over the flange 216. However, in contrast to the embodiment shown in FIGS. 1a and 1b, the sleeve of FIGS. 2a and 2b is held perpendicular to the plaster 218, that is perpendicular to the skin of a patient to which the plaster is secured.

Further embodiments of the fastener are illustrated in FIGS. 3, 4a, and 4b. In the embodiment of FIG. 3, the sleeve 310 is attached to a strap 312, which includes a hook-and-loop portion at each end 314 to enable the strap 312 to be secured at a selected width, for example around a patient's wrist. In order to secure the sleeve 310 to the strap 312, a flange 316 is supplied, which is securely attached to the collar of the sleeve 310. The flange 316 is secured to the strap 312 using an adhesive plaster as described above (not shown) or for example by ultrasound or heat welding the flange to the strap or by other fixing means.

The embodiment illustrated in FIGS. 4a and 4b includes a flange 416 secured around the sleeve 410 behind one of the collars 412, 414. The flange of FIGS. 4a and 4b is preferably secured to the collar using ultrasound welding. As illustrated in FIG. 4b, the flange includes at least one preformed aperture, preferably two, which may be used to secure the fastener to a patient, for example by suturing the fastener to the patient, the sutures being passed through the apertures in the flange 416.

A method of manufacturing a plurality of fasteners according to one embodiment is illustrated schematically in the flow chart of FIG. 5.

The method includes providing a supply of braided tubular sleeve 510, for example as part of a roll or cylinder. The supply includes a length of sleeve at least 1 metre in length, but is likely to be much longer than this, preferably of the order of 100 s of metres, when a new supply is brought into the manufacturing process.

A portion of braided tubular sleeve is provided from the supply 512. The length of the portion will depend on the length of the final fastener it is desired to create, however it is unlikely to be longer than 15 cm, more likely less than 10 cm, preferably around 5 cm or less. The length of the portion is related to the thickness of the sleeve; wider sleeves will tend to be made into longer fasteners to provide sufficient grip on wider lines. The length of the portion is also related to the intended use of the fastener since some medical uses, for example where the patient is expected to be moved a lot (e.g. use in a military situation or by paramedics) can be expected to put more strain on the fastener than others, for example neonatal care.

The method then includes providing a collar around the sleeve at at least one end of the portion 514 and the braided tubular sleeve is sealed within the collar 516.

The process then determines whether there is a further length of tubular sleeve on the supply 518. If so, the process continues by forming a further fastener in the same way as just described for the first fastener.

The collar is ultrasound-welded to the braided sleeve to ensure a secure fixation between the collar and the sleeve. An insert may be provided within the sleeve to compress the ends of the braid against the inner walls of the collar and hold the sleeve in position while the welding takes place. The collar and at least the portion of the sleeve lying within the collar are directed within ultrasound welding apparatus and waves at ultra-sonic frequencies are applied to the collar and sleeve. The waves are targeted to fall on, or to be focused on, the collar and the portion of the sleeve within the collar. This is to prevent any undesirable ultrasound welding of the sleeve outside the collar. In particular, the apparatus is arranged to prevent strands of the braided sleeve from being welded to each other, which would prevent necessary compression and extension of the sleeve.

A further collar is then secured to the other end of the sleeve to form the fastener. The further collar may be threaded onto the sleeve together with the first collar and both collars may be welded to the sleeve as part of the same process. Alternatively, the first collar may be welded, the portion of sleeve cut, and the second collar then welded to the other end of the portion of sleeve.

Once the fastener has been created in the manner described above, it may be secured to attachment means, such as adhesive material, to form fasteners such as those described herein.

In particular, in one embodiment, one of the collars includes an enlarged flange section. This is placed onto an adhesive plaster and positioned near to the edge of the plaster or close to a cut-out section. A second piece of adhesive plaster, which is larger than the flange, is then placed over the flange and secured onto the first piece of plaster, holding the flange in place on the first adhesive plaster.

For additional security, the flange itself may also have an adhesive substance applied to one or both of its surfaces. For example an adhesive substance may be sprayed onto the lower surface of the flange before it is placed onto the first adhesive plaster. This may be sufficient to hold the flange onto the plaster however, for security, it is preferable for the second adhesive plaster to be provided over the flange.

In some embodiments, different fixing means may be provided as an alternative or in addition, to secure the flange to the plaster. Depending on the materials from which the flange and plaster are made, the flange and plaster may be ultrasound welded or heat sealed together. Further, fixing means such as rivets, which may also plastic, may be provided to hold the flange onto the adhesive plaster.

Figure 6:
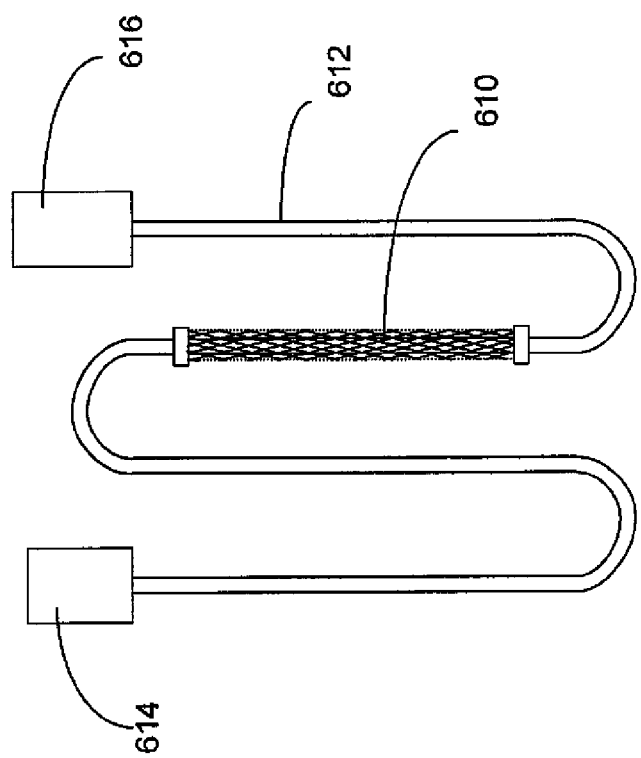
FIG. 6 illustrates a fastener according to a further embodiment.

A further embodiment of a fastener is illustrated in FIG. 6, which is a schematic illustration of a giving set, as part of which a fastener may be provided. The giving set includes a tube 612 for supplying fluid, for example saline solution, to a patient. As part of the manufacturing process, a braided tubular sleeve 610 is passed onto the sleeve by compressing the sleeve longitudinally, to widen the braid of the sleeve and sliding the sleeve 610 onto the tube 612.

Connectors (illustrated schematically in FIG. 6) 614, 616 are then attached to each end of the tube 612. It is noted that the connectors 614, 616 are larger than the collars provided at each end of the sleeve 610 and are therefore larger than the maximum diameter to which the sleeve 610 can widen. Therefore, the sleeve cannot pass over the connectors 614, 616 and cannot be removed from the tube 612 once the connectors have been added to each end.

Therefore, it is advantageous to add the sleeve to the giving set during the manufacturing and assembly process. The whole assembly can then be provided in a sterilised pack to medical practitioners. The sleeve then provides a convenient means by which the giving set can be attached with respect to a patient.

It will be clear to the skilled person that the method and apparatus described above are non-limiting embodiments and variations may be provided within the scope of the claims, which now follow.

The invention claimed is:

1. A medical or surgical apparatus comprising a sealed sterile pack containing:
   a line for supplying a fluid to or removing a fluid from a patient;
   a connector positioned at each end of the line; and
   a fastener comprising a braided tubular sleeve surrounding the line and positioned between the connectors for securing the line with respect to a patient, the braided tubular sleeve comprising a substantially rigid collar at each end of the sleeve;
   wherein pushing the collars towards each other along the longitudinal axis of the sleeve shortens and widens the sleeve, allowing the sleeve to slide along the line;
   wherein the sleeve is biased to an elongate position so that releasing the collars causes the sleeve to lengthen and grip the line; and
   wherein the maximum diameter of each connector is greater than the internal diameter of each of the collars so that the collars do not fit over either connector and the braided tubular sleeve is retained on the line;
   wherein, in use, the braided tubular sleeve is elongated and is configured to have a first end for fixing adjacent to the patient and a second end for arranging proximal to medical equipment coupled to the line;
   wherein an enlarged flange is secured to the first collar at the first end of the braided tubular sleeve, the enlarged flange having a plane defined by a major surface of the enlarged flange;
   an adhesive plaster for securing the fastener with respect to a patient is secured to the enlarged flange, the adhesive plaster having a plane defined by a major surface of the adhesive plaster; and
   the longitudinal axis of the elongate braided tubular sleeve is arranged parallel to the plane of the adhesive plaster and the plane of the enlarged flange.

2. The apparatus of claim 1 wherein:
   a first one of said substantially rigid collars is coupled to the sleeve at the first end of the sleeve; and
   a second one of said substantially rigid collars is coupled to the sleeve at the second end of the sleeve.

3. The apparatus of claim 1 wherein:
   the adhesive plaster comprises a first layer of adhesive plaster and a second layer of adhesive plaster; and
   the enlarged flange is coupled to the first layer of the adhesive plaster by the second layer of the adhesive plaster, the second layer of adhesive plaster being arranged over the enlarged flange.

4. The apparatus of claim 1 wherein the enlarged flange and the first collar are manufactured using a common material.

5. The apparatus of claim 1 wherein the enlarged flange is coupled to the first collar using at least one of:

ultrasound welding;
high-frequency welding; and heat-sealing and/or wherein the enlarged flange is moulded integrally with the first substantially rigid collar.

6. The apparatus of claim 1 wherein the adhesive plaster comprises one of a sterile medical or surgical plaster, and a pre-applied adhesive coating.

7. The apparatus of claim 1 wherein the elongate braided tubular sleeve comprises a plurality of braided strands.

8. The apparatus of claim 1 wherein the adhesive plaster comprises a pre-formed cut-out adjacent to the first end of the elongate braided tubular sleeve.

9. The apparatus of claim 1 wherein the lateral force required to separate the adhesive plaster from the patient, applied substantially parallel to the longitudinal axis of the elongate braided tubular sleeve, is greater than 1N.

10. The apparatus of claim 1 wherein the line comprises a tube.

11. A method of forming a medical or surgical apparatus comprising:
providing a line for supplying a fluid to or removing a fluid from a patient;
sliding a braided tubular sleeve onto the line, wherein the braided tubular sleeve is provided by a fastener having a first end and a second end, the first end configured to be fixed adjacent to the patient, in use, and the second end configured to be arranged, in use, proximal to medical equipment coupled to the line, and the fastener comprises a substantially rigid collar at each end of the sleeve, and an enlarged flange secured to the first collar at the first end of the braided tubular sleeve, the enlarged flange having a plane defined by a major surface of the enlarged flange;
and an adhesive plaster configured to secure the fastener with respect to a patient secured to the enlarged flange, the adhesive plaster having a plane defined by a major surface of the adhesive plaster;
wherein in use the longitudinal axis of the elongate braided tubular sleeve is arranged parallel to the plane of the adhesive plaster, and
wherein sliding comprises:
pushing the collars towards each other along the longitudinal axis of the sleeve to shorten and widen the sleeve;
sliding the sleeve onto the outer surface of the line; and
releasing the collars to enable the sleeve to return to a biased elongate position, causing the sleeve to grip the line;
attaching a connector to each end of the line, wherein the maximum diameter of each connector is greater than the maximum internal diameter of either collar so that the collars do not fit over either connector and the braided tubular sleeve is retained on the line; and
sealing the apparatus within a sterile container.

12. A medical or surgical apparatus comprising a sealed sterile pack containing:
a line for supplying fluid to or removing fluid from a patient;
a fastener for securing the line with respect to a patient;
wherein the fastener comprises:
an elongate braided tubular sleeve for receiving the line therethrough, the sleeve having a first end for fixing adjacent to the patient, in use, and a second end for arranging, in use, proximal to medical equipment coupled to the line;
a first substantially rigid collar coupled to the elongate braided tubular sleeve at the first end of the elongate braided tubular sleeve;
a second substantially rigid collar coupled to the elongate braided tubular sleeve at the second end of the elongate braided tubular sleeve;
wherein the sleeve is configured to be shortened and widened to allow the sleeve to slide along the line in response to the collars being pushed towards each other along the longitudinal axis;
wherein the sleeve is biased to an elongate position so that releasing the collars causes the sleeve to lengthen and grip the line; and
an enlarged flange for coupling with the first substantially rigid collar;
a stop for positioning on the line, the maximum diameter of the stop being greater than the internal diameter of at least one of the collars so that the at least one collar does not fit over the stop and the elongate braided tubular sleeve is retained on the line;
an enlarged flange secured to the first collar at the first end of the sleeve, the enlarged flange having a plane defined by a major surface of the enlarged flange; and
an adhesive plaster for securing the fastener with respect to a patient secured to the enlarged flange, the adhesive plaster having a plane defined by a major surface of the adhesive plaster;
wherein the longitudinal axis of the elongate braided tubular sleeve is arranged parallel to the plane of the adhesive plaster in use.

13. The medical or surgical apparatus of claim 12 comprising at least two stops.

* * * * *